United States Patent [19]

Serban et al.

[11] Patent Number: 4,655,819
[45] Date of Patent: Apr. 7, 1987

[54] QUINOXALINYLOXY PHENOXY PROPRIONIC ACID DERIVATIVES AS SELECTIVE HERBICIDES

[75] Inventors: Alexander Serban, Doncaster; Keith G. Watson, Box Hill North; Grame J. Farquharson, Reservoir, all of Australia

[73] Assignee: ICI Australia Limited, Victoria, Australia

[21] Appl. No.: 334,384

[22] Filed: Dec. 24, 1981

[30] Foreign Application Priority Data

Jul. 17, 1979 [AU] Australia ................ PD9617
Apr. 11, 1980 [AU] Australia ................ PE3093
Jan. 12, 1981 [AU] Australia ................ PE7201

[51] Int. Cl.$^4$ ............... A01N 43/60; C07D 241/52; C07D 241/44
[52] U.S. Cl. .............................. 71/92; 544/354
[58] Field of Search ..................... 71/92; 544/354

[56] References Cited

U.S. PATENT DOCUMENTS 4,248,618 12/1981 Serban ........................ 71/92

FOREIGN PATENT DOCUMENTS 23785    2/1981  European Pat. Off. ........... 544/354
42750   12/1981  European Pat. Off. ........... 544/354
56-16475  2/1981  Japan ........................ 544/354
56-46868  4/1981  Japan ........................ 544/354
56-57769  5/1981  Japan ........................ 544/354
56-97275  8/1981  Japan ........................ 544/354

OTHER PUBLICATIONS

Derwent for Belgian 881,815, 8-20-80.

Primary Examiner—Mark L. Berch
Attorney, Agent, or Firm—Cushman, Darby & Cushman

[57] ABSTRACT

The invention concerns novel compounds of the formula I

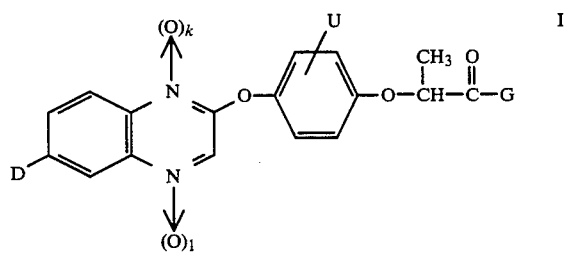

wherein:
D and U are independently chosen from halogen, methyl and halomethyl;
G is chosen from hydroxy, alkoxy, alkenyloxy, alkynyloxy, alkylthio, alkenylthio, alkynylthio, cycloalkoxy and the group OM wherein M is an alkali metal or alkaline earth metal ion; and
k and l are independently chosen from 0 and 1.

The compounds are herbicides and in further embodiments the invention provides processes for the preparation of compounds of formula I, intermediates useful in the preparation of compounds of formula I, herbicidal compositions containing as active ingredient a compound of formula I, and processes for severely damaging or killing unwanted plants by applying to the plants or to the growth medium of the plants and effective amount of a compound of formula I.

9 Claims, No Drawings

QUINOXALINYLOXY PHENOXY PROPRIONIC ACID DERIVATIVES AS SELECTIVE HERBICIDES

This application is a continuation-in-part of 06/164,933 filed July 1, 1980.

This invention relates to organic compounds having biological activity and in particular to organic compounds having herbicidal properties, to processes for the preparation of such compounds, to intermediates useful in the preparation of such compounds and to herbicidal compositions and processes utilizing such compounds.

We have now found a new class of quinoxalines which exhibit biological activity, and in particular herbicidal activity.

Accordingly the invention provides a compound of formula I:

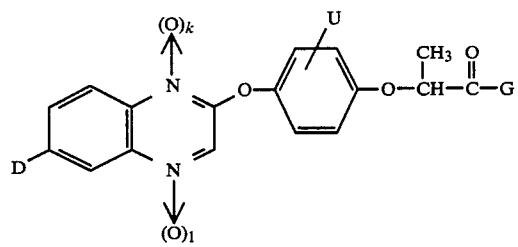

or a salt thereof wherein:

D and U are independently chosen from the group consisting of halogen, methyl and halomethyl;

G is chosen from the group consisting of hydroxy, mercapto, $C_1$ to $C_{10}$ alkoxy, $C_2$ to $C_{10}$ alkenyloxy, $C_2$ to $C_{10}$ alkynyloxy, $C_1$ to $C_{10}$ alkylthio, $C_2$ to $C_{10}$ alkenylthio, $C_2$ to $C_{10}$ alkynylthio, $C_3$ to $C_7$ cycloalkoxy and the group OM wherein M is an alkali metal or alkaline earth metal ion; and k and l are independently chosen from 0 and 1.

In the compounds of formula I the 2-carbon atom of the propionate group is asymmetrically substituted and therefore the compounds of formula I are optically active. The present invention includes the individual stereo isomers of such compounds, mixtures of those stereo isomers and the racemic mixture of stereo isomers.

Preferred D include fluorine, chlorine, bromine, iodine and trifluoromethyl. More preferred D is chlorine.

Preferred U include a fluorine, chlorine, bromine or iodine atom in the 2-position of the phenyl ring. More preferred U is 2-fluoro.

Preferred G include hydroxy, $C_1$ to $C_6$ alkoxy, $C_2$ to $C_6$ alkenyloxy, $C_2$ to $C_6$ alkynyloxy, cyclohexyloxy and the group OM wherein M is an alkali metal ion. More preferred G include hydroxy and $C_1$ to $C_6$ alkoxy.

Preferred k and l are 0.

Examples of compounds embraced by the invention include:

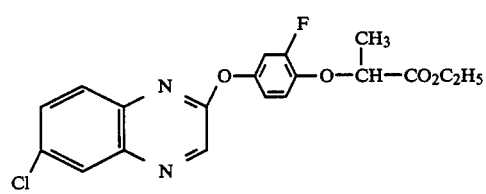

-continued

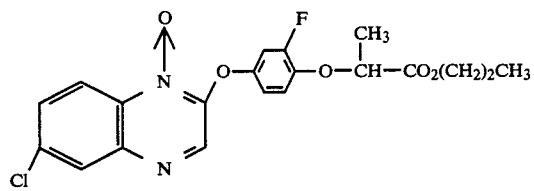

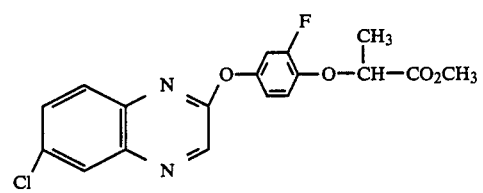

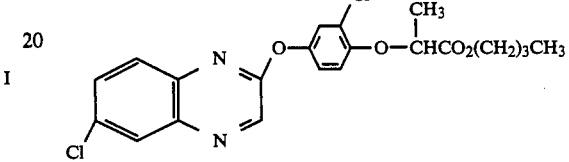

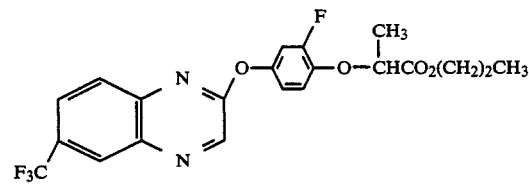

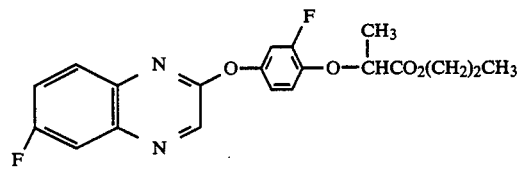

Specific examples of compounds of the invention include those detailed in Table 1 below.

TABLE 1

| | | | |
|---|---|---|---|
| Compound No | D | U | G |
| 1 | Cl | 2-F | $C_2H_5O$ |
| 7 | Cl | 2-F | $CH_3(CH_2)_2O$ |
| 8 | Cl | 2-F | $CH_3(CH_2)_3O$ |
| 9 | Cl | 2-F | HO |
| 10 | Br | 2-F | $C_2H_5O$ |
| 11 | Br | 2-F | $CH_3(CH_2)_2O$ |
| 12 | Br | 2-F | $CH_3(CH_2)_3O$ |
| 13 | Br | 2-F | HO |
| 14 | F | 2-F | $C_2H_5O$ |
| 15 | F | 2-F | $CH_3(CH_2)_2O$ |
| 16 | F | 2-F | $CH_3(CH_2)_3O$ |
| 17 | Cl | 3-F | $C_2H_5O$ |

The compounds of the invention may be prepared by a variety of methods and in a further aspect the invention provides methods for the preparation of the compounds of formula I.

Compounds of formula I wherein G is not hydroxy may be prepared from the acid of formula Ib (I; G=OH) by, for example, neutralisation of the acid with a base to give an acid salt or esterification of the acid with an alcohol or thiol to give an acid ester (SCHEME A). Processes known in the art for the preparation of acid salts and acid esters may be adapted, without undue experimentation, to prepare compounds of the invention of formula I from compounds of the invention of formula Ib.

SCHEME A

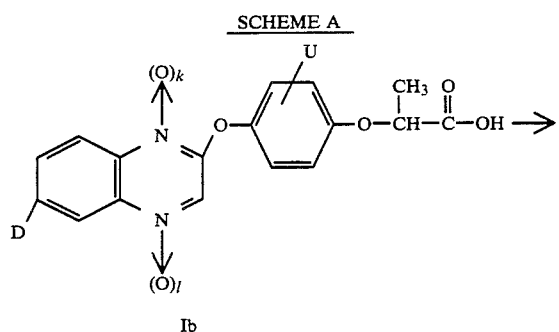

Ib

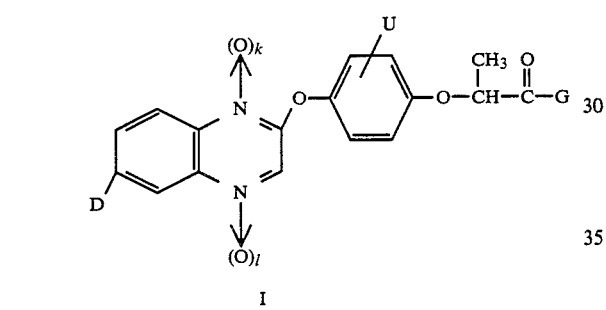

I

N-oxides of the invention of formula I wherein k and/or l is 1 may be prepared from compounds of the invention of formula I wherein k and/or l is 0 by oxidation. Processes known in the art for the conversion of quinoxalines to quinoxaline N-oxides, for example oxidations using persulfates, peroxides, peracids or peresters, may be adapted without undue experimentation, to prepare N-oxides of the invention.

Compounds of formula I wherein D, U, G, k and l are as hereinbefore defined may be prepared by the condensation of a phenol of formula IX with a compound of formula X wherein hal is chlorine, bromine or iodine, preferably in the presence of an alkaline material; according SCHEME B.

SCHEME B

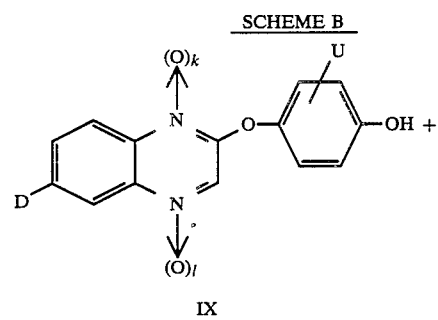

IX

-continued
SCHEME B

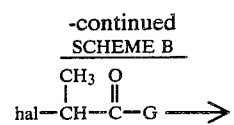

X

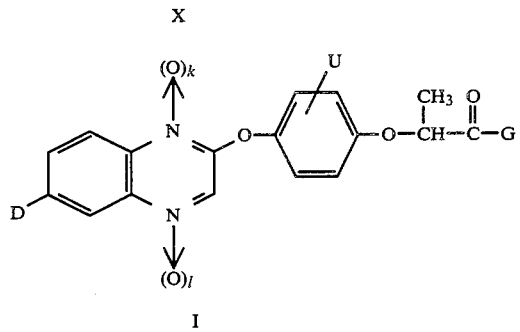

I

Compounds of formula I may also be prepared by:
(a) the condensation of the appropriate quinoxaline derivative of formula V, wherein L is a leaving group (for example, alkylsulfony, chlorine, bromine or iodine) with the appropriate phenol of formula VI according to SCHEME C; or

SCHEME C

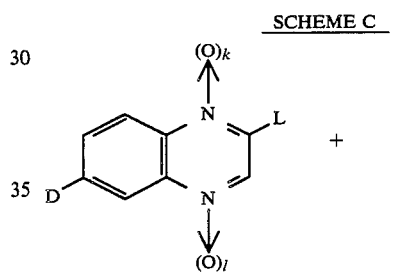

V

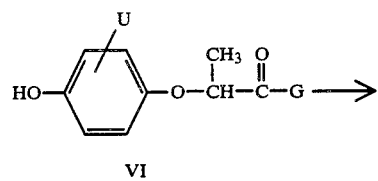

VI

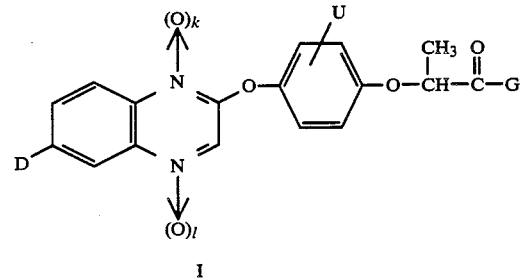

I (b) the following steps in sequence:
(i) the condensation of the appropriate quinoloxaline derivative of formula V, wherein L is a leaving group (for example, alkylsulfonyl, chlorine, bromine or iodine) with the appropriate compound of formula VII, wherein Q is hydroxy or $C_1$ to $C_6$ alkoxy to give a compound of formula VIII wherein Q is hydroxy or $C_1$ to $C_6$ alkoxy;

(ii) the dealkylation of the compound of formula VIII prepared in step (i) above wherein Q is $C_1$ to $C_6$ alkoxy to give a compound of formula IX; and
(iii) the condensation of the product of formula IX obtained in step (i) or step (ii) above with a compound of formula X according to the process described for SCHEME B above (steps (i) and (ii) are shown in SCHEME D); or cording to the process described for SCHEME D step (ii) above; and
(iii) the condensation of the product of formula IX obtained in step (i) or step (ii) above with a compound of formula X according to the process described for SCHEME B above (step (i) is shown in SCHEME E).

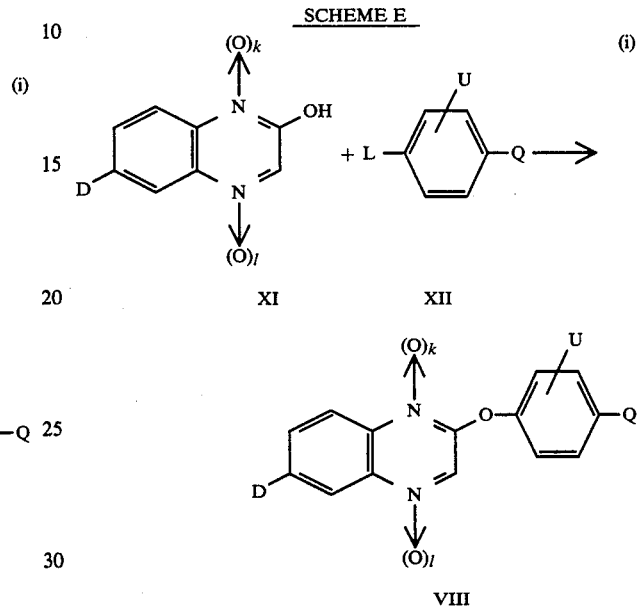

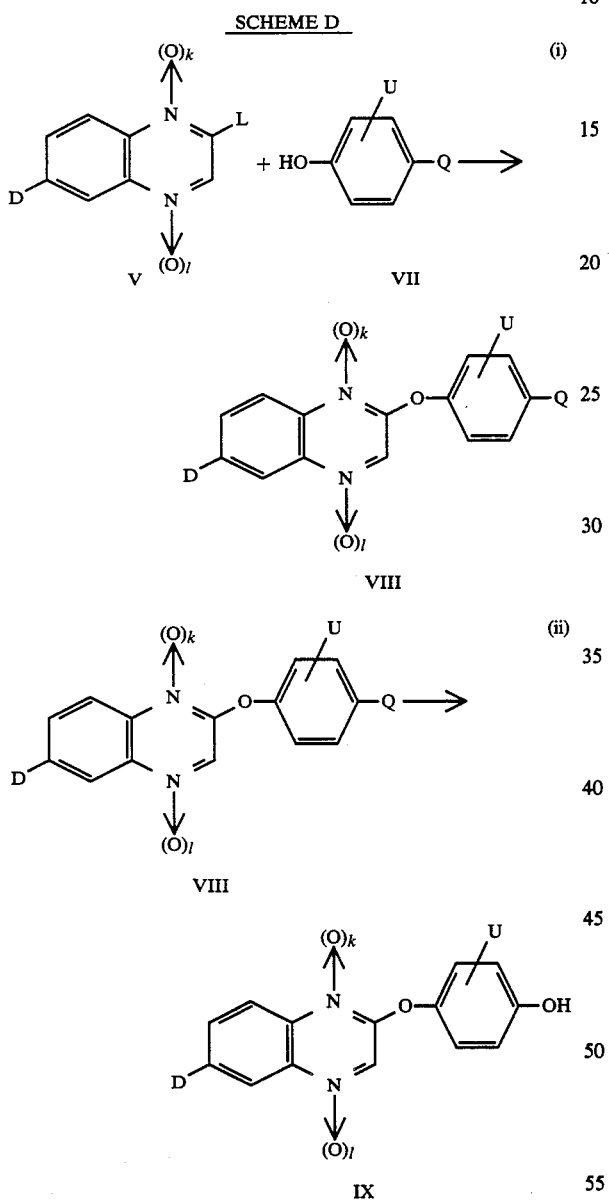

(c) the following steps in sequence:
(i) the condensation of the appropriate quinoxaline derivative of formula XI with the appropriate benzene derivative of formula XII wherein L is a leaving group (for example, alkylsulfonyl, chlorine, bromine or iodine) and Q is hydroxy or $C_1$ to $C_6$ alkoxy, to give a compound of formula VIII wherein Q is as hereinbefore defined;
(ii) the dealkylation of the compound of formula VIII prepared in step (i) above wherein Q is $C_1$ to $C_6$ alkoxy to give a compound of formula IX ac- The condensation reaction illustrated in SCHEMES B to E and outlined above are preferably carried out in the presence of an alkaline material and preferably in the presence of a solvent. Suitable alkaline materials include alkali metal and alkaline earth metal hydroxides and carbonates such as sodium hydroxide, potassium hydroxide, sodium carbonate and potassium carbonate. Suitable solvents include ketones such as, for example, acetone, methyl ethyl ketone and methyl isobutyl ketone, and dipolar aprotic solvents such as, for example, dimethylformamide, dimethylacetamide, dimethylsulfoxide, N-methylpyrrolidone, hexamethylphosphoramide and sulfolan.

The reaction conditions required to effect the condensation reactions illustrated in SCHEMES B, C, D and E and outlined above vary according to the nature of the reactants and the solvent used. In general the reaction is facilitated by the application of heat and usually a reaction temperature in the range of 40° to 150° C. and reaction time of between 0.5 and 20 hours is satisfactory. However, higher or lower reaction temperatures and/or shorter or longer reaction times may be used if desired.

The dealkylation reactions illustrated in SCHEMES D and E and outlined in paragraphs (b)(ii) and (c)(ii) above may be effected using a variety of reagents known in the art. For example, aryl-alkyl ethers may be cleaved using reagents such as pyridine hydrochloride, hydriodic acid, hydrobromic acid, sodium thioethoxide in dimethylformamide, acetyl p-toluene-sulphonate, sodium or potassium iodide in formac or acetic acid, lithium iodide in 2,4,6-collidine and boron tribromide. Reaction times and reaction conditions vary widely depending on the dealkylation agent used and the ether to be cleaved. The reaction conditions generally employed when using the above "ether-cleavage" reagents are known to those skilled in the art and may be adapted without undue experimentation to effect the "ether-cleavage" reactions illustrated in SCHEMES D and E and outlined in paragraph (b)(ii) and (c)(ii) above.

The compounds of formula VIII

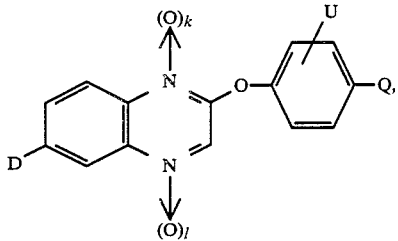

which are useful intermediates in the preparation of compounds of formula I, are also believed to be novel compounds. Therefore, in a further embodiment the invention provides compounds of formula VIII wherein D, U, k, l and Q are as hereinbefore defined.

The compounds of formula I are active as herbicides and therefore, in a further aspect the invention provides a process for severely damaging or killing unwanted plants which process comprises applying to the plants, or to the growth medium of the plants, an effective amount of a compound of formula I as hereinbefore defined.

Generally speaking the compounds of formula I are herbicidally effective against a variety of plants. However, certain of the compounds of the invention are selectively active against monocotyledonous plants, dicotylendonous plants being relatively unaffected by rates of application of the compounds of the invention which are severely damaging or lethal to other plant species.

Moreover, certain of the compounds of formula I are selectively active within the group of monocotyledonous plants and may be used at a rate sufficient to kill or severely damage monocotyledonous weeds in a monocotyledonous cereal crop.

Therefore, in yet a further aspect the invention provides a process for selectively controlling the growth of weeds in crops which process comprises applying to the crop, or to the growth medium of the crop, a compound of formula I, as hereinbefore defined, in an amount sufficient to severely damage or kill the weeds but insufficient to damage the crop substantially.

The compounds of formula I may be applied directly to the plant (post-emergence application) or to the soil before the emergence of the plant (pre-emergence application). However, the compounds are, in general, more effective when applied to the plant post-emergence.

The compounds of formula I may be used on their own to inhibit the growth of, severely damage, or kill plants but are preferably used in the form of a composition comprising a compound of the invention in admixture with a carrier comprising a solid or liquid diluent. Therefore, in yet a further aspect the invention provides plant growth inhibiting, plant damaging, or plant killing compositions comprising a compound of formula I as hereinbefore defined and an inert carrier therefor.

Compositions according to the invention include both dilute compositions, which are ready for immediate use, and concentrated compositions, which require to be diluted before use, usually with water. Preferably the compositions contain from 0.01% to 90% by weight of the active ingredient. Dilute compositions ready for use preferably contain from 0.01 to 2% of active ingredient, while concentrated compositions may contain from 20 to 90% of active ingredient, although from 20 to 70% is usually preferred.

The solid compositions may be in the form of granules, or dusting powders wherein the active ingredient is mixed with a finely divided solid diluent, eg kaolin, bentonite, kieselguhr, dolomite, calcium carbonate, talc, powdered magnesia, Fuller's earth and gypsum. They may also be in the form of dispersible powders or grains, comprising a wetting agent to facilitate the dispersion of the powder or grains in liquid. Solid compositions in the form of a powder may be applied as foliar dusts.

Liquid compositions may comprise a solution or dispersion of an active ingredient in water optionally containing a surface-active agent, or may comprise a solution or dispersion of an active ingredient in a water-immiscible organic solvent which is dispersed as droplets in water.

Surface-active agents may be of the cationic, anionic, or non-ionic type. The cationic agents are, for example, quaternary ammonium compounds (eg cetyltrimethylammonium bromide). Suitable anionic agents are soaps; salts of aliphatic mono esters of sulphuric acid, for example, sodium lauryl sulphate; and salts dodecylbenzenesulphonate, sodium, calcium, and ammonium lignosulphonate, butylnaphthalene sulphonate, and a mixture of the sodium salts of diisopropyl- and triisopropylnaphthalenesulphonic acid. Suitable non-ionic agents are the condensation products of ethylene oxide with fatty alcohols such as oleyl alcohol and cetyl alcohol, or with alkylphenols such as octyl- or nonyl-phenol or octyl-cresol. Other non-ionic agents are the partial esters derived from long chain fatty acids and hexitol anhydrides, for example sorbitan monolaurate; the condensation products of the partial ester with ethylene oxide; and the lecithins.

The aqueous solutions or dispersions may be prepared by dissolving the active ingredient in water or an organic solvent optionally containing wetting or dispersing agent(s) and then, when organic solvents are used, adding the mixture so obtained to water optionally containing wetting or dispersing agent(s). Suitable organic solvents include, for example, ethylene dichloride, isopropyl alcohol, propylene glycol, diacetone alcohol, toluene, kerosene, methylnaphthalene, the xylenes and trichloroethylene.

The compositions for use in the form of aqueous solutions or dispersions are generally supplied in the form of a concentrate containing a high proportion of the active ingredient, and the concentrate is then diluted with water before use. The concentrates are usually required to withstand storage for prolonged periods and after such storage, to be capable of dilution with water to form aqueous preparations which remain homogeneous for a sufficient time to enable them to be applied by conventional spray equipment. Concentrates conveniently contain 20–90%, preferably 20–70%, by weight of the active ingredient(s). Dilute preparations ready for use may contain varying amounts of the active ingredient(s) depending upon the intended purpose; amounts of 0.01% to 10.0% and preferably 0.1% to 2%, by weight of active ingredient(s) are normally used.

A preferred form of concentrated composition comprises the active ingredient which has been finely divided and which has been dispersed in water in the presence of a surface-active agent and a suspending agent. Suitable suspending agents are hydrophilic colloids and include, for example, polyvinylpyrrolidone and sodium carboxymethylcellulose, and the vegetable gums, for example gum acacia and gum tragacanth. Preferred suspending agents are those which impart thixotropic properties to, and increase the viscosity of the concentrate. Examples of preferred suspending agents include hydrated colloidal mineral silicates, such as montmorillonite, beidellite, nontronite, hectorite, saponite, and saucorite. Bentonite is especially preferred. Other suspending agents include cellulose derivatives and polyvinyl alcohol.

The rate of application of the compounds of the invention will depend on a number of factors including, for example, the compound chosen for use, the identity of the plants whose growth is to be inhibited, the formulations selected for use and whether the compound is to be applied for foliage or root uptake. As a general guide, however, an application rate of from 0.005 to 20 kilograms per hectare is suitable while from 0.01 to 5 kilograms per hectare may be preferred.

The compositions of the invention may comprise, in addition to one or more compounds of the invention, one or more compounds not of the invention but which possess biological activity. For example, as hereinbefore indicated the compounds of the invention are in general substantially more effective against monocotyledonous plants or grass species than against dicotyledonous plants or broad-leaved species. As a result, in certain applications the herbicidal use of the compounds of the invention alone may be sufficient to protect a crop. Accordingly in yet a still further embodiment the invention provides a herbicidal composition comprising a mixture of at least one herbicidal compound of formula I as hereinbefore defined with at least one other herbicide.

The other herbicide may be any herbicide not having the formula I. It will generally be a herbicide having a complementary action. For example, one preferred class is of mixtures comprising a herbicide active against broad-leaved weeds. A second preferred class is of mixtures comprising a contact herbicide.

Examples of useful complementary herbicides include:

A. benzo-2,1,3-thiadiazin-4-one-2,3-dioxides such as 3-isopropylbenzo-2,1,3-thiadiazin-4-one-2,2-dioxide (common name bentazon);

B. hormone herbicides and in particular the phenoxyalkanoic acids such as 4-chloro-2-methylphenoxy acetic acid (common name MCPA), 2-(2,4-dichlorophenoxy)propionic acid (common name dichlorprop), 2,4,5-trichlorophenoxyacetic acid (common name 2,4,5-T), 4-(4-chloro-2-methylphenoxy)butyric acid (common name MCPB), 2,4-dichlorophenoxyacetic acid (common name 2,4-D), 4-(2,4-dichlorophenoxy)butyric acid (common name 2,4-DB), 2-(4-chloro-2-methylphenoxy)propionic acid (common name mecoprop), and their derivatives (eg salts, esters, amides and the like);

C. 3-[4-(4-halophenoxy)phenyl]-1,1-dialkylureas such as 3-[4-(4-chlorophenoxy)phenyl]-1,1-dimethylurea (common name chloroxuron);

D. dinitrophenols and their derivatives (eg acetates) such as 2-methyl-4,6-dinitrophenol (common name DNOC), 2-tertiarybutyl-4,6-dinitrophenol (common name dinoterb), 2-secondarybutyl-4,6-dinitrophenol (common name dinoseb) and its ester dinoseb acetate;

E. dinitroaniline herbicides such as N',N'-diethyl-2,6-dinitro-4-trifluoromethyl-m-phenylenediamine (common name dinitriamine), 2,6-dinitro-N,N-dipropyl-4-trifluoromethylaniline (common name trifluralin) and 4-methylsulfonyl-2,6-dinitro-N,N-dipropylaniline (common name nitralin);

F. phenylurea herbicides such as N'-(3,4-dichlorophenyl)-N,N-dimethylurea (common name diuron) and N,N-dimethyl-N'-[3-(trifluoromethyl)phenyl]urea (common name fluometuron);

G. phenylcarbamoyloxyphenylcarbamates such as 3-[(methoxycarbonyl)amino]phenyl(3-methylphenyl)-carbamate (common name phenmedipham) and 3-[(ethoxycarbonyl)amino]phenyl phenylcarbamate (common name desmedipham);

H. 2-phenylpyridazin-3-ones such as 5-amino-4-chloro-2-phenylpyridazin-3-one (common name pyrazon);

I. uracil herbicides such as 3-cyclohexyl-5,6-trimethyleneuracil (common name lenacil), 5-bromo-3-sec-butyl-6-methyluracil (common name bromacil) and 3-tert-butyl-5-chloro-6-methyluracil (common name terbacil);

J. triazine herbicides such as 2-chloro-4-ethylamino-6-(iso-propylamino)-1,3,5-triazine (common name atrazine), 2-chloro-4,6-di(ethylamino)-1,3,5-triazine (common name simazine) and 2-azido-4-(iso-propylamino)-6-methylthio-1,3,5-triazine (common name aziprotryne);

K. 1-alkoxy-1-alkyl-3-phenylurea herbicides such as 3-(3,4-dichlorophenyl)-1-methoxy-1-methylurea (common name linuron), 3-(4-chlorophenyl)-1-methoxy-1-methylurea (common name monolinuron) and 3-(4-bromo-4-chlorophenyl)-1-methoxy-1-methylurea (common name chlorobromuron);

L. thiolcarbamate herbicides such as S-propyl dipropylthiocarbamate (common name verolate);

M. 1,2,4-triazin-5-one herbicides such as 4-amino-4,5-dihydro-3-methyl-6-phenyl-1,2,4-triazine-5-one (common name metamitron) and 4-amino-6-tert-butyl 4,5-dihydro-3-methylthio-1,3,4-triazin-5-one (common name metribuzin);

N. benzoic acid herbicides such as 2,3,6-trichlorobenzoic acid (common name 2,3,6-TBA), 3,6-dichloro-2-methoxybenzoic acid (common name dicamba) and 3-amino-2,5-dichlorobenzoic acid (common name chloramben);

O. anilide herbicides such as N-butoxymethyl-α-chloro-2',6'-diethylacetanilide (common name butachlor), the corresponding N-methoxy compound (common name alachlor), the corresponding N-iso-propyl compound (common name propachlor) and 3',4'-dichloropropionanilide (common name propanil);

P. dihalobenzonitrile herbicides such as 2,6-dichlorobenzonitrile (common name dichlobenil), 3,5-dibromo-4-hydroxybenzonitrile (common name bromoxynil) and 3,5-diiodo-4-hydroxybenzonitrile (common name ioxynil).

Q. haloalkanoic herbicides such as 2,2-dichloropropionic acid (common name dalapon), trichloroacetic acid (common name TCA) and salts thereof;

R. diphenylether herbicides such as 4-nitrophenyl 2-nitro-4-trifluoromethylphenyl ether (common name fluorodifen), methyl 5-(2,4-dichlorophenoxy)-2-nitrobenzoate (common name bifenox), 2-nitro-5-(2-chloro-4-trifluoromethylphenoxy)benzoic acid and 2-chloro-4-trifluoromethylphenyl 3-ethoxy-4-nitrophenyl ether; and S. miscellaneous herbicides including N,N-dimethyldiphenylacetamide (common name diphenamid), N-(1-naphthyl)phthalamic acid (common name naptalam) and 3-amino-1,2,4-triazole.

Examples of useful contact herbicides include:

T. bipyridylium herbicides such as those in which the active entity is the 1,1'-dimethyl-4,4'-dipyridylium ion (common name paraquat) and those in which the active entity is the 1,1'-ethylene-2,2'-dipyridylium ion (common name diquat);

U. organoarsenical herbicides such as monosodium methanearsonate (common name MSMA); and V. amino acid herbicides such as N-(phosphonomethyl)glycine (common name glyphosphate) and its salts and esters.

The invention is now illustrated by, but in no way limited to, the following examples.

EXAMPLE 1

Ethyl 2-[2-Fluoro-4-(6-chloroquinoxalin-2-yloxy)phenoxy]-propionate (1)

(a) A solution of potassium persulphate (70 g, 0.26 mole) in water (1.5 l) was added slowly, with stirring, to a solution of 3-fluorophenol (29 g, 0.26 mole) and sodium hydroxide (52 g, 1.3 mole) in water (520 ml) so that the temperature of the mixture remained below 20° C. The dark solution was stirred overnight at room temperature and then acidified to Congo red with hydrochloric acid. The solution was then extracted with diethyl ether (3×200 ml) to remove unreacted phenol. The aqueous layer was made neutral and evaporated to dryness and the residue was extracted into 90% ethanol (700 ml) to give a solution of 2-fluoro-4-hydroxyphenyl potassium sulphate. The solution was concentrated to 250 ml, sodium hydroxide (12 g, 0.3 mole) in water (50 ml) was added and then the solution was boiled and stirred while benzyl chloride (35 g, 0.28 mole) was added dropwise. Heating was continued for a further 2 hours and then concentrated hydrochloric acid was added to Congo red and the mixture boiled for 2 hours. The mixture was concentrated under reduced pressure then diluted with water and extracted with ether. The ether extracts were dried (MgSO₄) and evaporated to give the crude product. The product was purified by chromatography on silica gel with methylene chloride elution to give 2-fluoro-4-benzyloxyphenol (12.5 g, 25%), m.p. 67° C.

A mixture of 2-fluoro-4-benzyloxyphenol (11.85 g, 0.054 mole), ethyl 2-bromopropionate (9.83 g, 0.054 mole), anhydrous potassium carbonate (8.20 g, 0.059 mole) and ethyl methyl ketone (200 ml) was stirred and refluxed for 3 hours. The solvent was removed on a rotary evaporator and the residue partitioned between methylene chloride and water. The organic layer was dried (MgSO₄) and evaporated to give a pale brown oil (15.5 g) which slowly solidified. Recrystallization from ethanol gave the product, ethyl 2-[2-fluoro-4-(benzyloxy)phenoxy]-propionate, as nearly colourless crystals (13.0 g; 75% ), mp 63° C.

10% Palladium on charcoal (1.5 g) was added to a solution of ethyl 2-(2-fluoro-4-benzyloxyphenoxy)propionate (13 g) in ethanol (250 ml) and the stirred suspension was placed under hydrogen at atmospheric pressure for 2 hours. The catalyst was removed by filtration and the filtrate evaporated under reduced pressure to give the product, ethyl 2-(2-fluoro-4-hydroxyphenoxy)-propionate, as a colourless oil (8.9 g, 95%). Proton magnetic resonance spectrum (CDCl₃, δ in ppm): 1.3, t, 3H (CH₂C$\underline{H}$₃); 1.6, d, 3H (—CHC$\underline{H}$₃); 4.25, q, 2H (OC$\underline{H}$₂CH₃); 4.7, q, 1H (—C$\underline{H}$CH₃); 6.4–7.1, m, 4H (O$\underline{H}$ and phenoxy ring).

(b) A mixture of 2,6-dichloroquinoxaline (0.99 g 0.005 mole), ethyl 2-(2-fluoro-4-hydroxyphenoxy)propionate (1.14 g, 0.005 mole), anhydrous potassium carbonate (0.76 g, 0.0055 mole) and dimethylformamide (20 ml) was stirred and heated at 100° C. for 2 hours. The mixture was cooled and then poured into water (200 ml) to give a white precipitate which was collected by filtration. Recrystallization from ethanol gave the product, ethyl 2-[2-fluoro-4-(6-chloroquinoxalin-2-yloxy)-phenoxy]propionate, as colourless crystals (1.3 g; 66%), mp 110° C. Proton magnetic resonance spectrum (CDCl₃, δ in ppm); 1.3, t, 3H (CH₂C$\underline{H}$₃); 1.7, d, 3H (CHC$\underline{H}$₃); 4.3, q, 2H (OC$\underline{H}$₂CH₃); 4.8, q, 1H (C$\underline{H}$CH₃); 6.9–7.5, m, 3H (phenoxy ring); 7.8, bs, 2H (C7, C8 of quinoxaline); 8.2, bs, 1H (C5 of quinoxaline); 8.8, s, 1H (C3 of quinoxaline).

EXAMPLE 2

Ethyl 2-[2-fluoro-4-(6-bromoquinoxalin-2-yloxy)phenoxy]-propionate (10) was prepared from 6-bromo-2-chloroquinoxaline and ethyl 2-(2-fluoro-4-hydroxyphenoxy)-propionate following essentially the same procedure as that described in Example 1 part (b). The title compound was obtained as colourless crystals mp 107°–108.6° C. and the assigned structure was characterised by nuclear magnetic resonance spectroscopy.

EXAMPLE 3

2-[2-Fluoro-4-(6-chloroquinoxalin-2-yloxy)phenoxy]-propionic acid (9)

Ethyl 2-[2-fluoro-4-(6-chloroquinoxalin-2-yloxy)-phenoxy]propionate (3.23 g; 8.27 mmole) was dissolved in a warm mixture of isopropanol (150 ml) and tetrahydrofuran (30 ml). The solution was allowed to cool to a temperature of 25° C. and a solution of sodium hydroxide (0.34 g) in water (10 ml) was added slowly with stirring. The reaction mixture was stirred at room temperature for a period of 10 minutes and then aqueous 2M sodium hydroxide (0.5 ml) was added and the solution was stirred at room temperature for 5 hours. The solvent was removed from the reaction mixture by evaporation under reduced pressure and the residue was dissolved in water. The aqueous solution was treated with aqueous 2M hydrochloric acid until acidic and the precipitated product was collected by filtration and air dried. The product was recrystallised from toluene to give the title compound (1.83 g; 61%), mp 132°–138° C. The assigned structure was confirmed by nuclear magnetic resonance spectroscopy.

EXAMPLE 4

2-[2-Fluoro-4-(6-bromoquinoxalin-2-yloxy)phenoxy]-propionic acid (13) was prepared from the corresponding ethyl ester by hydrolysis following essentially the same procedure as that described in Example 3. The assigned structure was confirmed by nuclear magnetic resonance spectroscopy.

EXAMPLE 5 n-Propyl 2-[2-fluoro-4-(6-chloroquinoxalin-2-yloxy)-phenoxy]-propionate (7)

(a) 2-[2-Fluoro-4-(6-chloroquinoxalin-2-yloxy)-phenoxy]-propionic acid (1.73 g; 4.77 mmole) was treated with thionyl chloride and the mixture was heated under reflux with stirring for a period of 5 hours. The excess thionyl chloride was removed by distillation under reduced pressure to give 2-[2-fluoro-4-(6-chloroquinoxalin-2-yloxy)phenoxy]-propionyl chloride as a straw coloured oil.

(b) 2-[2-Fluoro-4-(6-chloroquinoxalin-2-yloxy)-phenoxy]-propionyl chloride (0.9 g; 2.3 mmole) was dissolved in dry dichloromethane and the solution was added slowly with stirring to a cooled mixture of n-propanol (5 ml) and triethylamine (1 ml). The mixture was stirred at room temperature for a period of 4 hours and then the solvent was evaporated under vacuum and the residue was dissolved in dichloromethane. The solution was washed with water and the organic phase was dried over magnesium sulfate. The solution was filtered and the solvent was removed under vacuum to give a light brown oil (0.92 g; 95.3%). The product was crystallised from ethanol to give the title compound as a crystalline solid (0.58 g; 60.4%); mp 70°–72° C. The assigned structure was confirmed by nuclear magnetic resonance spectroscopy.

EXAMPLE 6

The following compounds were prepared from the appropriate acid and the appropriate alcohol following essentially the same procedure as that described in Example 5:

n-butyl 2-[2-fluoro-4-(6-chloroquinoxalin-2-yloxy)-phenoxy]propionate (8), solid, mp 56°–60.5° C.;
n-propyl 2-[2-fluoro-4-(6-bromoquinoxalin-2-yloxy)-phenoxy]propionate (11), solid, mp 63°–64.5° C.; and
n-butyl 2-[2-fluoro-4-(6-bromoquinoxalin-2-yloxy)-phenoxy]propionate (12), oil Each of the assigned structures was confirmed by nuclear magnetic resonance spectroscopy.

EXAMPLE 7 n-Propyl 2-[2-fluoro-4-(6-fluoroquinoxalin-2-yloxy)-phenoxy]-propionate (15)

(a) (i) A solution of potassium persulfate (70.0 g) in water (1.5 l) was added slowly with stirring to a solution of 2-fluorophenol (29.0 g) and sodium hydroxide (52.0 g) in water (520 ml) the reaction mixture being maintained at a temperature of 10° to 20° C. throughout the addition. The reaction mixture was stirred overnight at room temperature and then acidified with concentrated hydrochloric acid to Congo Red. The aqueous solution was extracted with diethyl ether (to remove any unreacted phenol) and then neutralized by the addition of an aqueous saturated solution of sodium hydrogen carbonate. The neutralized aqueous solution was evaporated to dryness to give a brown residue which was triturated with 90% ethanol (several times using 2 l of ethanol overall). The ethanolic extracts were filtered and the solvent evaporated to give an orange solid (58.0 g).

The solid was dissolved in a solution comprising a mixture of 90% ethanol (300 ml), water (100 ml) and sodium hydroxide (9.9 g). The mixture was heated to reflux and ethyl α-bromopropionate (44.8 g) was slowly added. The reaction mixture was heated under reflux for a period of 4½ hours. The mixture was cooled to 60°–70° C., acidified to Congo Red with concentrated hydrochloric acid and then heated under reflux for a further 2½ hours. The solution was cooled and the solvent was evaporated under vacuum to give a brown solid. The solid was treated with water and the aqueous mixture was extracted several times with diethyl ether. The combined etherial extracts were washed with water, dried over anhydrous magnesium sulfate, filtered and the ether was evaporated to give a brown oil (30.0 g).

The brown oil was dissolved in ethanol (150 ml), a solution of sodium hydroxide (5.3 g) in water (50 ml) was added and the mixture was stirred at a temperature of 50° C. for a period of 4 hours. The solvent was removed from the reaction mixture under vacuum and the residue was acidified with dilute hydrochloric acid. The mixture was extracted several times with diethyl ether and the combined etherial extracts were washed with water, dried over anhydrous magnesium sulfate, filtered, and the solvent removed under reduced pressure to give crude 2-(2-fluoro-4-hydroxyphenoxy)propionic acid (20.5 g; 39.6%).

(a) (ii) n-Propanol (35 ml) and concentrated sulfuric acid (6 drops) were added to a solution of crude 2-(2-fluoro-4-hydroxyphenoxy)propionic acid (8.6 g) in dichloroethane (13 ml). The mixture was heated under reflux with stirring for a period of 6.5 hours, cooled, and the solvent was evaporated under reduced pressure. The residue was treated with water and the aqueous mixture was extracted with dichloromethane. The organic phase was washed with a saturated aqueous solution of sodium hydrogen carbonate and then with water. The organic phase was dried over anhydrous magnesium sulfate, filtered and the solvent was evaporated under reduced pressure to give an oil (5.7 g; 54.8%). The oil was purified by vacuum distillation to give n-propyl 2-(2-fluoro-4-hydroxyphenoxy)propionate (3.7 g; 35.5%); bp 210°–220° C. at 0.1 mm Hg.

(b) A mixture of 2-chloro-6-fluoroquinoxaline (1.0 g; 5.48 mmole), n-propyl 2-(2-fluoro-4-hydroxyphenoxy)-propionate (1.33 g; 5.49 mmole), anhydrous potassium carbonate (0.8 g) and anhydrous dimethylformamide (40 ml) was stirred and heated at a temperature of 120° C. for a period of 3.5 hours. The solvent was evaporated from the reaction mixture under vacuum, the residue was treated with water and the mixture was extracted with diethyl ether. The etherial extract was washed with water, dried over anhydrous magnesium sulfate, filtered, and the solvent was evaporated under vacuum to give a brown oil. The product was purified by preparative thin layer chromatography over silica gel (eluant chloroform/ethanol, 95:5) to give the title compound (0.89 g; 41.8%) as a solid; mp 49°–51° C.

The assigned structure was confirmed by nuclear magnetic resonance spectroscopy and mass spectrometry.

EXAMPLE 8

The following compounds were prepared from the appropriate alkyl 2-(2-fluoro-4-hydroxyphenoxy)-propionate, prepared from the appropriate alcohol and 2-(2-fluoro-4-hydroxyphenoxy)propionic acid according to the procedure described in Example 7 part (a)(ii), and 2-chloro-6-fluoroquinoxaline following essentially the same procedure as that described in Example 8 part (b):

ethyl 2-[2-fluoro-4-(6-fluoroquinoxalin-2-yloxy)phenoxy]propionate (14), solid, mp 58°–59° C.; and n-butyl 2-[2-fluoro-4-(6-fluoroquinoxalin-2-yloxy)-phenoxy]propionate (16), solid; mp 57°–58° C.

Each of the assigned structures was confirmed by nuclear magnetic resonance spectroscopy.

EXAMPLE 9

Ethyl 2-[3-fluoro-4-(6-chloroquinoxalin-2-yloxy)-phenoxy]propionate (17) was prepared from 2-fluorophenol following the same procedure as that described in Example 1.

The first step yielded 3-fluoro-4-benzyloxyphenol as a colourless solid, mp 80° C.

Ethyl 2-(3-fluoro-4-benzyloxyphenoxy)propionate was obtained as colourless crystals, mp 77° C.

Ethyl 2-(3-fluoro-4-hydroxyphenoxy)propionate was obtained as a colourless oil. Proton magnetic resonance spectrum (CDCl$_3$; δ in ppm): 1.25 (t, 3H); 1.55 (d, 3H); 4.25 (q, 2H); 4.7 (q, 1H); 6.15 (br.s, 1H); 6.45–7.1 (m, 3H).

The title compound, ethyl 2-[3-fluoro-4-(6-chloroquinoxalin-2-yloxy)phenoxy]propionate was obtained as colourless crystals, mp 109° C.

EXAMPLE 10

Concentrated formulations of the compounds of the invention were prepared by:

(a) in the case of oils and waxy solids, dissolving the compound in toluene containing 7% v/v "Teric" N13 ("Teric" is a Trade Mark and "Teric" N13, a product of ethoxylation of nonylphenol, is available from ICI Australia Limted) and 3% v/v "Kemmat" SC15B ("Kemmat" is a Trade Mark and "Kemmat" SC15B is a formulation of calcium dodecylbenzene sulfonate); or (b) in the case of crystalline solids, adding 5 parts by weight of the compound and 1 part by weight of "Dyapol" PT ("Dyapol" is a Trade Mark and "Dyapol" PT is an anionic suspending agent) to 94 parts by weight of an aqueous solution containing 0.25% v/v of "Teric" N8 (a product of ethoxylation of nonylphenol) and ball-milling the mixture to produce a stable suspension. The emulsifiable concentrates and suspensions were then diluted with water to give an aqueous composition of the required concentration suitable for use in the evaluation of the pre-emergence and post-emergence herbicidal activity of the compounds of the invention.

EXAMPLE 11

The pre-emergent herbicidal activity of the compounds of the invention formulated as described in Example 10 was assessed by the following procedure.

The seeds of the test species were sown in rows 2 cm deep in soil contained in seed boxes. The monocotyledonous plants and the dicotyledonous plants were sown in separate boxes and after sowing the two boxes were sprayed with the required quantity of a composition of the invention. Two duplicate seed boxes were prepared in the same manner but were not sprayed with a composition of the invention and were used for comparison purposes. All the boxes were placed in a glasshouse, lightly watered with an overhead spray to initiate germination and then sub-irrigated as required for optimum plant growth. After three weeks the boxes were removed from the glasshouse and the effect of the treatment was visually assessed. The results are presented in Table 2 where the damage to plants is rated on a scale of from 0 to 3 where 0 represents from 0 to 25% damage, 3 represents 75 to 99% kill and 3+ represents 100% kill. A dash (-) means that no experiment was carried out.

The names of the test plants are as follows:

| | |
|---|---|
| Wh | Wheat |
| Ot | Wild Oats |
| Rg | Ryegrass |
| Jm | Japanese millet |
| P | Peas |
| Ip | Ipomea |
| Ms | Mustard |
| Sf | Sunflower |

TABLE 2
PRE-EMERGENCE HERBICIDAL ACTIVITY

| Compound No | Application Rate kg/ha | Wh | Ot | Rg | Jm | P | Ip | Ms | Sf |
|---|---|---|---|---|---|---|---|---|---|
| 1 | 1.0 | 3 | 3 | 3+ | 3+ | 0 | 0 | 0 | 0 |
| 1 | 0.5 | 1 | 3 | 3 | 3+ | 0 | 0 | 0 | 0 |
| 1 | 0.25 | 0 | 1 | 3 | 3+ | 0 | 0 | 0 | 0 |
| 17 | 5.0 | 2 | 1 | 3+ | 3+ | 0 | 0 | 0 | 0 |
| 17 | 1.0 | 1 | 0 | 3 | 3 | 0 | 0 | 0 | 0 |

EXAMPLE 12

The post-emergent herbicidal activity of the compounds of the invention formulated as described in Example 10 was assessed by the following procedure.

The seeds of the test species were sown in rows 2 cm deep in soil contained in seed boxes. The monocotyledonous plants and the dicotyledonous plants were sown in separate seed boxes in duplicate. The four seed boxes were placed in a glasshouse, lightly watered with an overhead spray to initiate germination and then subirrigated as required for optimum plant growth. After the plants had grown to a height of about 10 to 12.5 cm one box of each of the monocotyledonous plants and the dicotyledonous plants was removed from the glasshouse and sprayed with the required quantity of a composition of the invention. After spraying the boxes were returned to the glasshouse for a further 3 weeks and the effect of treatment was visually assessed by comparison with the untreated controls. The results are presented in Table 3 where the damage to plants is rated on a scale of from 0 to 3 where 0 represents 0 to 25% damage, 3 represents 75 to 99% kill and 3+ represents 100% kill. A dash (-) means that no experiment was carried out.

The names of the test plants are as follows:

| | |
|---|---|
| Wh | Wheat |
| Ot | Wild Oats |
| Rg | Ryegrass |
| Jm | Japanese millet |
| P | Peas |
| Ip | Ipomea |
| Ms | Mustard |

-continued

| | |
|---|---|
| Sf | Sunflower |† 
| Sb | Sugar beet |
| Rp | Rape |
| Ct | Cotton |
| Sy | Soy bean |
| Mz | Maize |
| Ww | Winter wheat |
| Rc | Rice |
| Sn | Senecio vulgaris |
| Ip | Ipomea purpurea |
| Am | Amaranthus retroflexus |
| Pi | Polygonum aviculare |
| Ca | Chenopodium album |
| Ga | Galium aparine |
| Xa | Xanthium pensylvanicum |
| Ab | Abutilon theophrasti |
| Co | Cassia obtusifolia |
| Av | Avena fatua |
| Dg | Digitaria sanguinalis |
| Al | Alopecurus myosuroides |
| St | Setaria viridis |
| Ec | Echinochloa crus-galli |
| Sh | Sorghum halepense |
| Ag | Agropyron repens |
| Cn | Cyperus rotundas |

TABLE 3

POST-EMERGENCE HERBICIDAL ACTIVITY

| Compound No | Application Rate kg/ha | Wh | Ot | Rg | Jm | P | Ip | Ms | Sf |
|---|---|---|---|---|---|---|---|---|---|
| 1 | 1.0 | 3+ | 3+ | 3+ | 3+ | 0 | 0 | 0 | 0 |
| 1 | 0.5 | 3+ | 3+ | 3+ | 3+ | 0 | 0 | 0 | 0 |
| 1 | 0.25 | 3 | 3+ | 3+ | 3+ | 0 | 0 | 0 | 0 |
| 17 | 5.0 | 3 | 2 | 3+ | 3+ | 0 | 0 | 0 | 0 |
| 17 | 1.0 | 2 | — | 3 | 3+ | 0 | 0 | 0 | 0 |

EXAMPLE 13

The compounds were formulated for test by mixing an appropriate amount with 5 ml of an emulsion prepared by diluting 160 ml of a solution containing 21.8 g per liter of "Span" 80 and 78.2 g per liter of "Tween" 20 in methylcyclohexanone to 500 ml with water. "Span" 80 is a Trade Mark for a surface-active agent comprising sorbitan monlaurate. "Tween" 20 is a Trade Mark for a surface-active agent comprising a condensate of sorbitan monolaurate with 20 molar proportions of ethylene oxide. Each 5 ml emulsion containing a test compound was then diluted to 40 ml with water and sprayed on to young pot plants (post-emergence test) of the species named in Table 4 below. Damage to test plants was assessed after 14 days on a scale of 0 to 5 where 0 is 0 to 20% damage and 5 is complete kill. In a test for pre-emergence herbicidal activity, seeds of the test plants were sown in a shallow slit formed in the surface of soil in fibre trays. The surface was then levelled and sprayed, and fresh soil then spread thinly over the sprayed surface. Assessment of herbicidal damage was carried out after 21 days using the same scale of 0 to 5 as the post-emergence test. In both cases the degree of herbicidal damage was assessed by comparison with untreated control plants. The results are given in Table 4 below. A dash (-) means that no experiment was carried out.

The names of the test plants were as follows:

TABLE 4

| Compound No. | APPLICATION Method | Rate (kg/ha) | Sb | Rp | Ct | Sy | Mz | Ww | Rc | Sn | Ip | Am | Pi | Ca | Ga | Xa | Ab | Co | Av | Dg | Al | St | Ec | Sh | Ag | Cn |
|---|---|---|---|---|---|---|---|---|---|---|---|---|---|---|---|---|---|---|---|---|---|---|---|---|---|---|
| 1 | PRE | 0.2 | 0 | 0 | 0 | 0 | 2 | 4 | 5 | 0 | 0 | 0 | — | 0 | — | 0 | 0 | 0 | 4 | 3 | 4 | 4 | 3 | 3 | 5 | 1 |
| 1 | PRE | 0.05 | 0 | 0 | 0 | 0 | 0 | 3 | 0 | 0 | 0 | 1 | — | 0 | — | 0 | 0 | 0 | 1 | 0 | 3 | 1 | 0 | 0 | 4 | 0 |
| 1 | PRE | 0.01 | — | — | — | — | 0 | 1 | 0 | — | — | — | — | — | — | — | — | — | 0 | 0 | 0 | 0 | 0 | 1 | 1 | 0 |
| 1 | POST | 0.2 | 1 | 2 | 0 | 1 | 4 | 4 | 5 | 1 | 0 | 1 | — | — | 0 | 0 | 0 | 0 | 5 | 5 | 5 | 5 | 5 | 5 | 4 | 0 |
| 1 | POST | 0.05 | 0 | 0 | 0 | 0 | 5 | 4 | 4 | 0 | 0 | 0 | — | — | 0 | 0 | 0 | 0 | 4 | 5 | 5 | 5 | 5 | 5 | 3 | 0 |
| 1 | POST | 0.01 | — | — | — | — | 4 | 4 | 0 | — | — | — | — | — | — | — | — | — | 4 | 3 | 3 | 4 | 4 | 4 | 2 | 1 |
| 10 | PRE | 0.025 | 0 | 0 | 0 | — | 1 | 3 | 2 | 1 | 0 | — | — | 0 | 0 | 0 | 0 | 0 | 0 | 0 | 2 | 0 | 0 | 0 | 4 | 0 |
| 10 | PRE | 0.01 | 0 | 0 | 0 | 0 | 0 | 1 | 0 | 0 | 0 | — | 0 | 0 | 0 | 0 | 0 | 0 | 0 | 0 | 0 | 0 | 0 | 0 | 4 | 0 |
| 10 | POST | 0.025 | 0 | 0 | 0 | 1 | 4 | 4 | 0 | 0 | 0 | — | 0 | 0 | — | — | — | — | 4 | 4 | 4 | 5 | 5 | 3 | 5 | 0 |
| 10 | POST | 0.01 | 0 | 0 | 0 | 1 | 2 | 3 | 0 | 0 | 0 | — | 0 | 0 | — | — | — | — | 3 | 4 | 3 | 2 | 5 | 2 | 0 | 0 |
| 14 | PRE | 0.02 | — | — | — | — | 0 | 3 | 3 | — | — | — | — | — | — | — | — | — | 0 | 2 | 2 | 0 | 1 | 0 | 2 | 0 |
| 14 | PRE | 0.01 | — | — | — | — | 1 | 1 | 1 | — | — | — | — | — | — | — | — | — | 0 | 0 | 1 | 0 | 0 | 0 | 1 | 0 |
| 14 | POST | 0.02 | — | — | — | — | 4 | 3 | 2 | — | — | — | — | — | — | — | — | — | 4 | 4 | 4 | 5 | 5 | 5 | 2 | 0 |
| 14 | POST | 0.01 | — | — | — | — | 4 | 3 | 1 | — | — | — | — | — | — | — | — | — | 4 | 3 | 4 | 3 | 5 | 5 | 0 | 0 |
| 17 | PRE | 2.0 | 0 | 0 | 0 | 0 | 4 | 5 | 5 | 0 | 0 | 0 | — | 0 | — | 0 | 0 | 0 | 3 | 4 | 5 | 5 | 5 | 5 | 5 | 1 |
| 17 | PRE | 0.5 | — | — | — | — | 4 | 4 | 4 | — | — | — | — | — | — | — | — | — | 3 | 5 | 5 | 5 | 5 | 4 | 5 | 2 |
| 17 | PRE | 0.05 | — | — | — | — | 1 | 0' | 0 | — | — | — | — | — | — | — | — | — | 1 | 3 | 3 | 0 | 0 | 3 | 3 | 0 |
| 17 | POST | 2.0 | 1 | 0 | 0 | 2 | 5 | 4 | 2 | 0 | 0 | 0 | — | — | 0 | 0 | 0 | 0 | 3 | 5 | 5 | 5 | 5 | 5 | 4 | 0 |
| 17 | POST | 0.5 | — | — | — | — | 5 | 4 | 4 | — | — | — | — | — | — | — | — | — | 2 | 4 | 3 | 4 | 5 | 5 | 2 | 0 |
| 17 | POST | 0.05 | — | — | — | — | 5 | 2 | 0 | — | — | — | — | — | — | — | — | — | 1 | 1 | 2 | 3 | 3 | 1 | 1 | 0 |

EXAMPLE 14

This example illustrates the selective herbicidal activity of the compounds of the invention.

The compounds were formulated and applied to the test species following the procedure described in Example 13. The species of test plant and the results are given in Tables 5 and 6 below. Damage to the test plants was assessed 26 days after treatment on a scale of 0 to 9 where 0 represents 0 to 10% damage and 9 represents 90 to 100% damage. A dash (-) means that no experiment was carried out.

TABLE 5

| Compound No | APPLICATION Method | Rate (kg/ha) | Crops | | | | Weeds | | | |
|---|---|---|---|---|---|---|---|---|---|---|
| | | | Pe | Rp | Sb | Lt | Av | Al | Bt | Ag |
| 1 | PRE | 0.4 | 1 | 0 | 0 | 2 | 2 | 8 | 6 | 8 |
| 1 | PRE | 0.2 | 0 | 0 | 0 | 1 | 2 | 5 | 1 | 3 |
| 1 | POST | 0.4 | 0 | 0 | 0 | — | 6 | 4 | 5 | 2 |
| 1 | POST | 0.2 | 0 | 0 | 0 | — | 3 | 3 | 2 | 2 |
| 7 | PRE | 0.4 | 0 | 0 | 0 | 0 | 6 | 9 | 4 | 9 |

TABLE 5-continued

| Com-pound No | APPLICATION Method | Rate (kg/ha) | TEST PLANT Crops | | | | Weeds | | | |
|---|---|---|---|---|---|---|---|---|---|---|
| | | | Pe | Rp | Sb | Lt | Av | Al | Bt | Ag |
| 7 | PRE | 0.2 | 0 | 0 | 0 | 0 | 6 | 7 | 2 | 6 |
| 14 | PRE | 0.4 | 0 | 0 | 0 | 0 | 8 | 9 | 7 | 9 |
| 14 | PRE | 0.2 | 0 | 0 | 0 | 0 | 9 | 9 | 8 | 9 |

The names of the Test Plants are as follows:

| | |
|---|---|
| Pe | Pea |
| Rp | Rape |
| Sb | Sugar beet |
| Lt | Lettuce |
| Av | *Avena fatua* |
| Al | *Alopecurus myosuroides* |
| Bt | *Bromus tectorum* |
| Ag | *Agropyron repens* |

TABLE 6

| Com-pound No | APPLICATION Method | Rate (kg/ha) | TEST PLANT Crops | | | Weeds | | | | |
|---|---|---|---|---|---|---|---|---|---|---|
| | | | Sy | Ct | To | Ec | Dg | St | Sh | Pm |
| 1 | PRE | 0.1 | 0 | — | 0 | 4 | 7 | 1 | 9 | 1 |
| 1 | PRE | 0.05 | — | — | 0 | 7 | 9 | 4 | 8 | 5 |
| 1 | PRE | 0.025 | 0 | 0 | 0 | 8 | 9 | 9 | 9 | 9 |
| 1 | POST | 0.1 | 0 | 0 | 0 | 9 | 9 | 9 | 9 | 9 |
| 1 | POST | 0.05 | 0 | 0 | 0 | 9 | 9 | 9 | 9 | 9 |
| 1 | POST | 0.025 | 0 | 0 | 0 | 9 | 9 | 8 | 9 | 9 |
| 7 | PRE | 0.2 | — | — | — | 9 | 9 | 9 | 7 | 9 |
| 7 | PRE | 0.1 | 0 | 0 | 0 | 9 | 8 | 7 | 5 | 9 |
| 7 | PRE | 0.05 | 0 | 1 | 0 | 8 | 7 | 6 | 3 | 8 |
| 14 | PRE | 0.2 | 0 | 1 | 0 | 9 | 8 | 9 | 8 | 9 |
| 14 | PRE | 0.1 | 0 | 0 | 0 | 9 | 8 | 9 | 6 | 9 |
| 14 | PRE | 0.05 | 0 | 0 | 0 | 9 | 8 | 8 | 4 | 9 |

The names of the Test Plants are as follows:

| | |
|---|---|
| Sy | Soyabean |
| Ct | Cotton |
| To | Tomato |
| Ec | *Echinochloa crus-galli* |
| Dg | *Digitaria sanguinalis* |
| St | *Setaria viridis* |
| Sh | *Sorghum halepense* |
| Pm | *Panicum maximum* |

We claim:
1. A compound of formula I

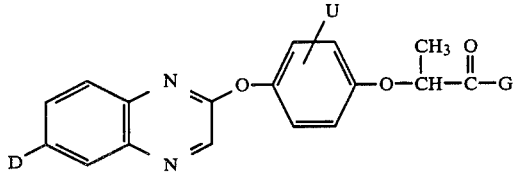

or a salt thereof wherein:
D is chosen from the group consisting of fluorine and chlorine;
U is fluorine substituted in the 2-position of the benzene ring; and
G is chosen from the group consisting of hydroxy, $C_1$ to $C_6$ alkoxy, $C_2$ to $C_6$ alkenyloxy, $C_2$ to $C_6$ alkynyloxy, cyclohexyloxy and the group OM wherein M is an alkali metal ion.

2. A process for severely damaging or killing unwanted plants which process comprises applying to said plants, or to the growth medium of said plants, an effective amount of a compound as defined according to claim 1.

3. A compound according to claim 1 wherein:
D is chosen from the group consisting of fluorine and chlorine;
U is fluorine substituted in the 2-position of the benzene ring; and
G is chosen from the group consisting of hydroxy and $C_1$ to $C_6$ alkoxy.

4. A compound according to claim 3 wherein:
D is chlorine;
U is fluorine substituted in the 2-position of the benzene ring; and
G is chosen from the group consisting of hydroxy, ethoxy, n-propoxy and n-butoxy.

5. The compound n-propyl 2-[2-fluoro-4-(6-chloroquinoxalin-2-yloxy)phenoxy]propionate.

6. The compound n-propyl 2-[2-fluoro-4-(6-fluoroquinoxalin-2-yloxy)phenoxy]propionate.

7. A process for selectively controlling the growth of monocotyledonous weeds in dicotyledonous crops which process comprises applying to said crop, or to the growth medium of said crop, a compound as defined according to claim 1 in an amount sufficient to severely damage or kill the weeds but insufficient to substantially damage the crop.

8. A herbicidal composition comprising as active ingredient an effective amount of a compound as defined according to claim 1 and a carrier therefor.

9. A process according to claim 2 or claim 7 wherein the compound is applied at a rate in the range from 0.005 to 20 kilograms per hectare.

* * * * *